United States Patent [19]

Marciel

[11] Patent Number: Plant 7,462

[45] Date of Patent: Mar. 5, 1991

[54] ROSE PLANT NAMED DEVSOLEAR

[75] Inventor: Stanley G. Marciel, Aptos, Calif.

[73] Assignee: DeVor Nurseries, Inc., Watsonville, Calif.

[21] Appl. No.: 383,419

[22] Filed: Jul. 24, 1989

[51] Int. Cl.[5] ..... A01H 5/00

[52] U.S. Cl. ..... Plt./15

[58] Field of Search ..... Plt./15

*Primary Examiner*—Howard J. Locker

*Attorney, Agent, or Firm*—Charles W. Rummler

[57] ABSTRACT

A new and distinct rose variety distinguished by the solid yellow orange coloration of its medium sized blooms which are grown on long, strong, upright stems of about 144 cm. in length, the plant having a continuous blooming habit with a profuse production of blooms from Spring to late Mid-Season and blooming profusely under glass from Fall until near Spring. The plant itself being an upright, free branching bush having a vigorous and rapid growth rate and its blooms having an on plant lasting quality of about 14 days.

1 Drawing Sheet

BACKGROUND OF THE NEW PLANT

This new rose variety originated as a seedling resulting from a hybrid produced by me at Pleasanton, Calif. by crossing an unnamed seedling with the variety Excitement (U.S. Plant Pat. No. 4,412) as the pollen parent with the object of producing a bright yellow rose which would not fade and being long lasting as a cut flower. This particular seedling was selected for propagation because of its clean and overall yellow orange flower carried on a long, strong stem of a plant appearing to have a vigorous growth habit and other advantageous characteristics. I propagated this plant by budding at Pleasanton with such satisfactory results that propagation in that manner was carried through several successive generations which assured me that the distinctive characteristics of this variety would hold true from generation to generation and appeared to be firmly fixed.

DESCRIPTION OF THE DRAWING

My new rose plant is illustrated by the accompanying photographic drawing which shows the flower in several stages of development, the principal subject being a flower in full bloom, the colors shown being as nearly true to that herein specified as is reasonably possible to obtain by professional photographic procedures.

DESCRIPTION OF THE NEW VARIETY

The following is a detailed description of my new rose plant based upon observation of outdoor grown plants at Pleasanton, Calif., with the color designations being according to The R.H.S. Colour Chart published by the Royal Horticultural Society of London, England.

THE PLANT

Origin: Seedling.

Parentage:

*Seed parent.*—Unnamed and unpatented.

*Pollen parent.*—The variety Excitement (U.S. Plant Pat. No. 4,412).

Classification:

*Botanic.*—Hybrid rose plant.

*Commercial.*—Greenhouse rose.

Form: Upright bush.

Height: Average.

Growth: Vigorous and sturdy with rapid growth rate.

Branching character: Free branching.

Main stem length: About 144 cm.

*Color.*—Yellow-green, 146 C.

Foliage:

*Quantity.*—Abundant.

*Number.*—6 or 7 leaves from last flower cut.

*Leaf size.*—Averages about 13 cm. long and about 9 cm. wide.

*Leaf type.*—Odd pinnate with three or five leaflets.

*Leaflets.*—Size: About 59 mm. long and about 33 mm. wide. Shape: Ovate with serrated margin. Texture: Medium leathery. Aspect: Medium glossy. Color: Upper side — Green, 137 A. Underside — Yellow green, 147 B. Petioles: About 21 mm. long.

Ribs and veins: Prominent on underside of leaf.

Thorns: This plant does have thorns.

*Size.*—About 6 mm. long.

*Color.*—Red, 51 B.

THE BUD

Mature bud size: Medium.

*Diameter.*—About 58 mm.

*Length.*—About 30 mm.

Shape: Urn-shaped.

Rate of opening: Slow.

Color of petals:

*When sepals first divide.*—Yellow, 13 A.

*When petals begin to unfurl.*—Yellow orange, 14A.

Sepals:

*Number.*—Five.

*Shape.*—Ovate with acuminate tip.

*Character.*—The sepals are hooded over the bud before dividing and curl back when the flower opens.

*Color.*—Inside — Green, 138D. Outside — Yellow green, 144B.

Calyx:

*Shape.*—Funnel-shaped.

*Size.*—Medium width and length.

*Splitting.*—Calyx does not split.

*Aspect.*—Smooth.

Peduncle:

*Length.*—About 75 mm. in average.
*Character.*—Slender and erect.
*Color.*—Yellow green, 145 A.

THE FLOWER

Blooming habit: Continuous and profusely from Spring to Fall. After late Fall, continuing to bloom profusely under glass.
Size of bloom: Medium.
*Diameter.*—About 80 to 85 mm.
*Depth.*—About 35 mm.
Borne: Singly.
Shape:
*When bloom first opens*—cup-shaped with high center.
*When bloom matures.*—somewhat flattened cup-shaped.
Petalage:
*Number.*—About 26 to 28.
*Arrangement.*—Imbricated.
*Shape.*—Orbicular with entire margins and acuminate tip.
*Texture.*—Leathery.
*Appearance.*—Satiny.
*Color.*—Outer petals: Entire body — Yellow orange, 14 A. Reverse side — Lemon yellow, 13 A. Inside petals: Entire body — Canary yellow, 9 A. Reverse side — 9 B.
Petaloids:
*Number.*—Two.
*Size.*—About 10 to 15 mm.
*Color.*—Canary yellow, 9 A.
Peduncle:
*Length.*—About 75 mm.
*Color.*—145 A.
*Character.*—Sturdy and upright.
Persistence: The flowers hang on and dry.
Fragrance: Slight.
Lasting quality:

*On plant.*—12 to 14 days.
*As cut flower.*—10 to 12 days in vase keeping.

THE REPRODUCTIVE ORGANS

Stamens:
*Number.*—94 to 106.
*Arrangement.*—Slightly introsed.
*Anthers.*—Size: About 4 mm. Color: Buttercup yellow, 15 B.
*Filaments.*—Length: From about 2 to 9 mm. Color: Canary yellow, 9 B.
*Pollen.*—Color: Lemon Yellow, 14 B.
Pistils:
*Number.*—About 60 to 65.
*Styles.*—Length: About 5 mm. Color: Canary yellow, 9 D.
*Stigmas.*—Color: Spiraea red, 63 C.
Character of the ovaries: Covered with silvery white hairs with styles unattached to each other and the tube is ovoid.

THE FRUIT

Fertility: The fruit is very fertile with the hip averaging about 12 seeds.
Shape: Round.
Color at maturity: Tangerine orange, 24 B.

The flower of this plant most nearly resembles that of Excitement (U.S. Plant Pat. No. 4,412) but with smaller flowers having more petals, a deeper yellow coloration; and longer lasting as a cut flower.

I claim:

1. The new and distinctive rose plant variety substantially as herein shown and described, particularly distinguished by its profuse and continuous production of medium sized flowers with a clear yellow orange and canary yellow coloration and having a vigorous upright rapid and free branching growth habit.

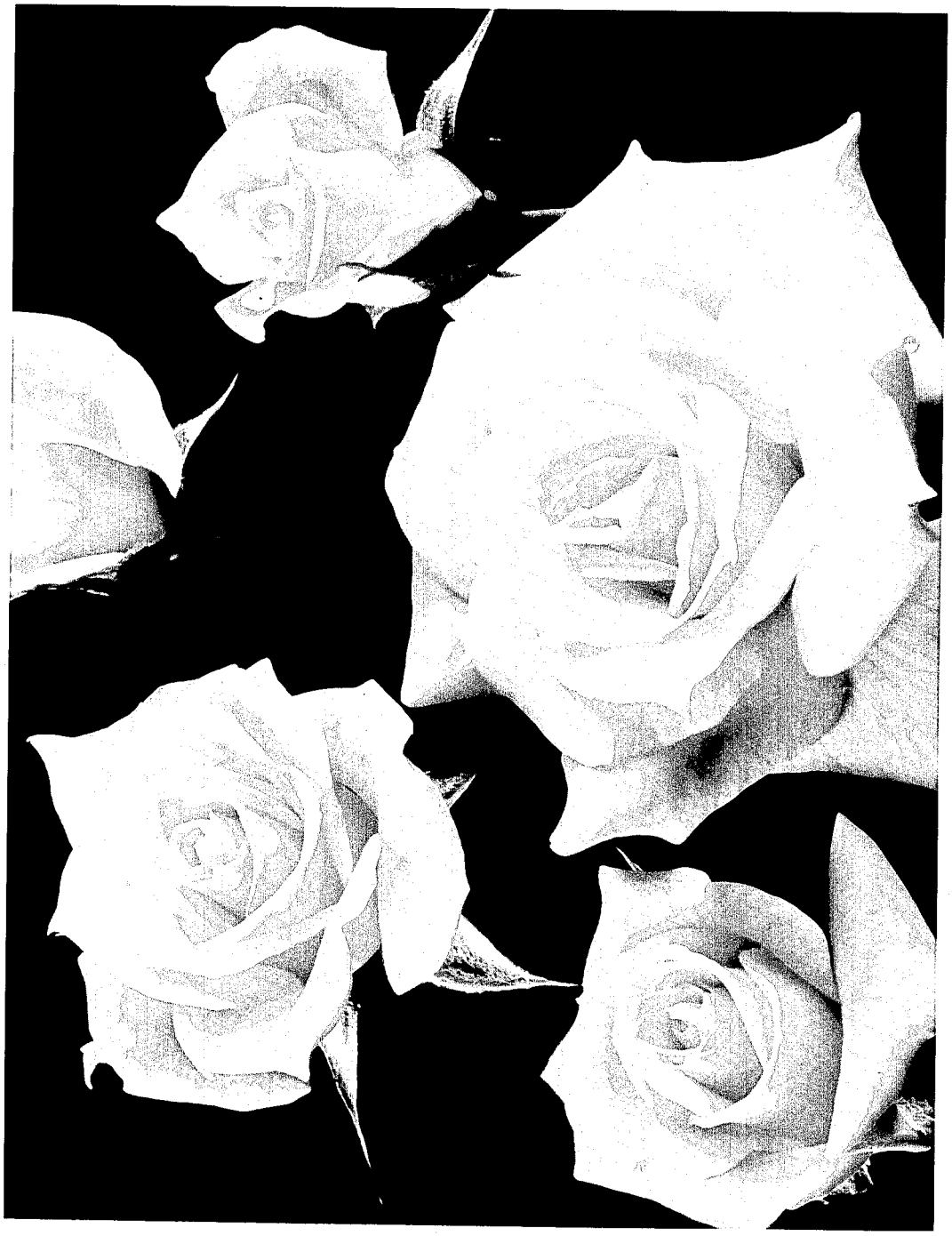

* * * * *